United States Patent
Sendai

(10) Patent No.: US 8,170,646 B2
(45) Date of Patent: *May 1, 2012

(54) DYNAMIC RADIOGRAPHIC IMAGE OBTAINING METHOD AND APPARATUS

(75) Inventor: Tomonari Sendai, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/886,865

(22) Filed: Sep. 21, 2010

(65) Prior Publication Data

US 2011/0009743 A1    Jan. 13, 2011

Related U.S. Application Data

(62) Division of application No. 11/090,145, filed on Mar. 28, 2005, now Pat. No. 7,826,888.

(30) Foreign Application Priority Data

Mar. 26, 2004  (JP) .................. 2004-092712

(51) Int. Cl.
*A61B 5/05* (2006.01)
*A61B 6/00* (2006.01)

(52) U.S. Cl. ............................. 600/428; 378/8

(58) Field of Classification Search .................. 600/428; 378/8, 62, 95; 382/130

See application file for complete search history.

(56) References Cited

U.S. PATENT DOCUMENTS

| 4,182,311 | A | 1/1980 | Seppi et al. |
| 6,233,478 | B1 | 5/2001 | Liu |
| 6,370,217 | B1 | 4/2002 | Hu et al. |
| 6,393,091 | B1 | 5/2002 | Slack et al. |
| 7,042,975 | B2 | 5/2006 | Heuscher |
| 7,050,537 | B2 | 5/2006 | Tsujii |
| 7,826,888 | B2 * | 11/2010 | Sendai .................. 600/428 |
| 2005/0147285 | A1 | 7/2005 | Tago et al. |

FOREIGN PATENT DOCUMENTS

| JP | 07-193751 A | 7/1995 |
| JP | 2003245272 | 9/2003 |
| WO | 03/083777 A2 | 10/2003 |

* cited by examiner

*Primary Examiner* — Michael Rozanski
(74) *Attorney, Agent, or Firm* — Sughrue Mion, PLLC

(57) ABSTRACT

A method and apparatus for obtaining a dynamic radiographic image with enhanced resolution, in which an electrocardiogram of a subject is obtained, and five time phases are allocated to each cardiac beat period (1 second). The initial X-ray irradiation is performed at $1^{st}$ time phase of $1^{st}$ beat to obtain a radiographic image. Thereafter, X-ray irradiations are performed sequentially at $2^{nd}$ time phase of $2^{nd}$ beat, at $3^{rd}$ time phase of $3^{rd}$ beat, at $4^{th}$ time phase of $4^{th}$ beat, and at $5^{th}$ time phase of $5^{th}$ beat to obtain respective radiographic images. The five radiographic images obtained are combined at the time interval of 0.2 seconds to be displayed as a motion image. The time interval between the irradiations of the X-ray is 1.2 seconds, so that image signals corresponding to $1^{st}$ to $5^{th}$ time phases may be obtained with high resolution.

11 Claims, 4 Drawing Sheets

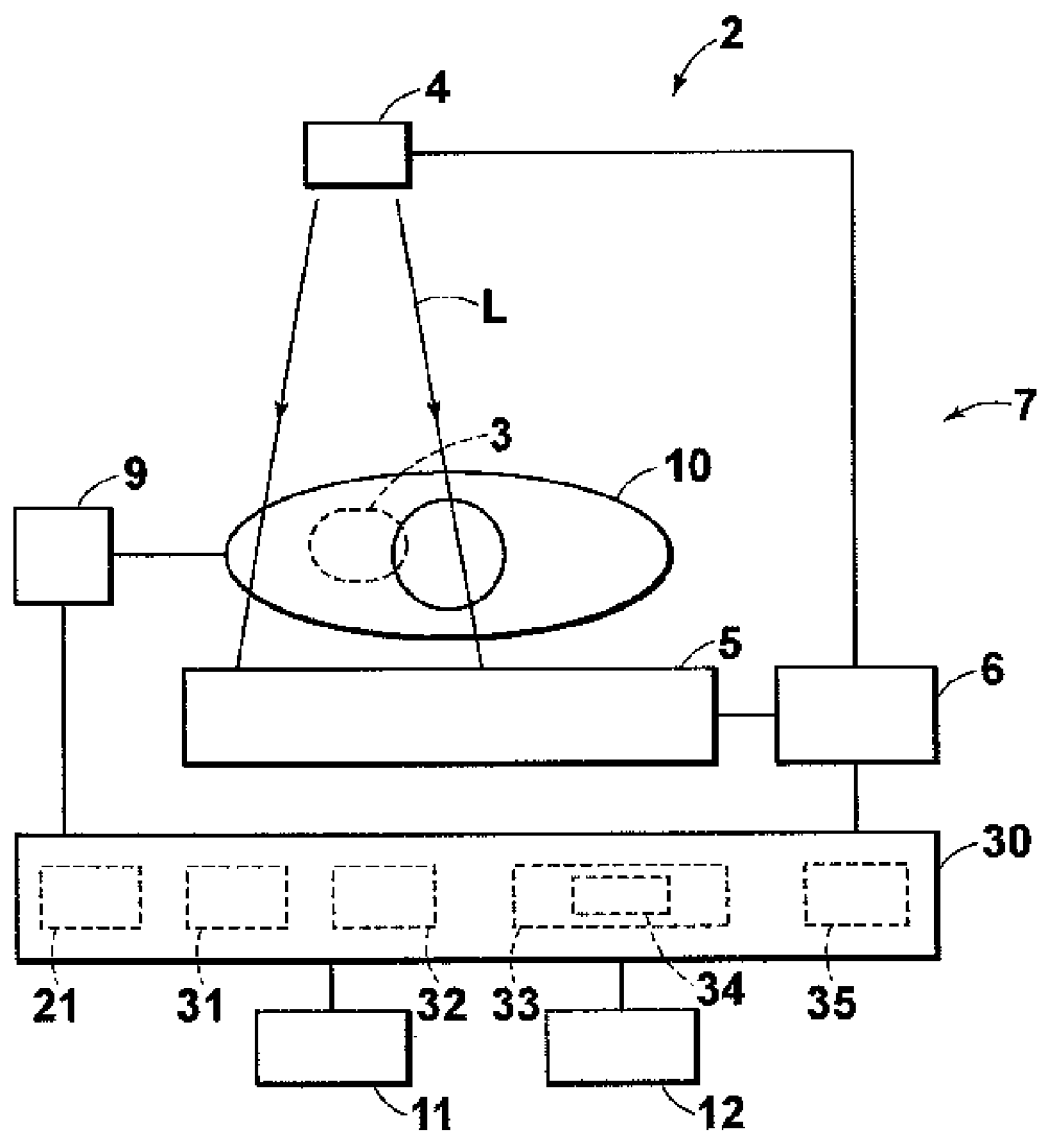

DYNAMIC RADIOGRAPHIC IMAGE OBTAINING METHOD AND APPARATUS

This application is a divisional of U.S. application Ser. No. 11/090,145, now U.S. Pat. No. 7,826,888, filed Mar. 28, 2005, which claims priority to JP Application No. 2004-092712, filed Mar. 26, 2004, each of which is incorporated herein by reference in its entirety.

BACKGROUND OF THE INVENTION

1. Field of the Invention

The present invention relates to a dynamic radiographic image obtaining method and apparatus for obtaining a dynamic radiographic image of a moving subject. More specifically, the present invention relates to a dynamic radiographic image obtaining method and apparatus for obtaining a dynamic radiographic image of a periodically moving subject.

2. Description of the Related Art

In the field of radiography, such as medical radiography for diagnosis and the like, or industrial radiography for non-destructive inspection for devices and the like, various radiographic image obtaining systems are known. These systems detect the radiation passed through the subject to obtain radiographic image information carried by the radiation as image signals.

For example, if radiation is irradiated on a storage phosphor, a part of the radiation energy is stored, and photostimulated luminescence is emitted in proportion to the energy stored therein when excitation light, such as visible light or a laser beam, is irradiated thereon. A radiographic image obtaining system that uses a storage phosphor sheet made of storage phosphor (photostimulable phosphor) layered on a substrate is widely put into practical use, which is known as computed Radiography (CR). In the system, the radiation passed through the subject, such as a human body, is received by the phosphor sheet to store the radiographic image information carried by the radiation, and excitation light, such as a laser beam is irradiated on the phosphor sheet to produce photostimulated luminescence, which is then converted to image signals through photoelectric conversion.

Another type of radiographic image obtaining system that stores radiographic image information, and reads out the information as image signals is also proposed. The system uses an electrostatic recording medium for recording a radiographic image as a latent charge image. In the system, the radiographic image information is recorded as a latent charge image by storing an amount of charges which is proportional to the radiation dosage irradiated thereon in the storage section of the electrostatic recording medium as the charges forming the latent image, and image signals are read out from the storage section according to the latent charge image. For this type radiation image obtaining system, several different types are proposed. For example, from the aspect of charge reading process, TFT reading system and optical reading system are proposed. TFT reading system converts charges forming a latent image stored in the storage section to image signals by driving TFTs to scan the recording medium, and outputs the converted image signals. Optical reading system converts the charges forming a latent image stored in the storage section to image signals by irradiating a reading electromagnetic wave (generally, visible light), and outputs the image signals.

In addition, several dynamic radiographic image obtaining methods for obtaining a dynamic radiographic image of a moving subject using these radiographic image obtaining systems are proposed by the applicant or others as described, for example, in Japanese Unexamined Patent Publication No. 7 (1995)-193751.

In the dynamic radiographic image obtaining apparatus described in Japanese Unexamined Patent Publication No. 7 (1995)-193751, however, a large amount of image signals needs to be read out for obtaining a radiographic image having high resolution, which requires a prolonged reading time, so that it is difficult to obtain a multitude of high-resolution radiographic images in a short period of time. Consequently, radiographic images are obtained as low resolution images when a dynamic image is obtained, and as high resolution images only when still images are obtained. Thus, the apparatus has a problem that detailed functional diagnosis by the observer is difficult to perform even if the dynamic radiographic image is displayed as a motion image on the monitor or the like.

The present invention has been developed in view of the circumstances described above, and it is an object of the present invention to provide a dynamic radiographic image obtaining method and apparatus capable of enhancing the resolution of a dynamic radiographic image.

SUMMARY OF THE INVENTION

The dynamic radiographic image obtaining method of the present invention is a method for obtaining a dynamic radiographic image of a periodically moving subject by repeating a radiographic image obtaining process of irradiating radiation on the subject and detecting the radiation passed through the subject a plurality of times, the method comprising the steps of:

detecting a dynamic signal of the subject;

allocating a plurality of time phases to each of predetermined periods of the dynamic signal;

obtaining a radiographic image of the subject at a time phase that differs from one predetermined period to another;

storing the radiographic image obtained with the time phase information correlated therewith; and obtaining the dynamic radiographic image of the subject by arranging the radiographic images obtained in the order of the time phases, each being stored correlated with each corresponding radiographic image, from the radiographic image obtained at the time phase closest to the starting point of the predetermined periods of the dynamic signal.

The dynamic radiographic image obtaining apparatus of the present invention is an apparatus for obtaining a dynamic radiographic image of a periodically moving subject, having an image obtaining means for obtaining a radiographic image of the subject by irradiating radiation on the subject and detecting the radiation passed through the subject, and obtaining the dynamic radiographic image of the subject by obtaining a plurality of radiographic images of the subject by the image obtaining means, wherein the apparatus further comprises:

a dynamic signal detecting means for detecting a dynamic signal of the subject;

a control means for allocating a plurality of time phases to each of predetermined periods of the dynamic signal detected by the dynamic signal detecting means, and controlling the image obtaining means such that a radiographic image of the subject is obtained at a time phase that differs from one predetermined period to another;

a storing means for storing the radiographic image obtained with the time phase information correlated therewith; and a dynamic image generating means for generating the dynamic image of the subject by arranging the radiographic images obtained in the order of the time phases, each being stored correlated with each corresponding radiation image, from the radiographic image obtained at the time phase closest to the starting point of the predetermined periods of the dynamic signal.

The referent of "allocating a plurality of time phases to each of predetermined periods" as used herein may include allocation of a plurality of time phases to each period, or allocation of a plurality of time phases to every two or more periods. For example, five time phases comprising the $1^{st}$ to $5^{th}$ time phases may be allocated to a single period, or they may be allocated to every two or three periods.

The referent of "obtaining a radiographic image of the subject at a time phase that differs from one predetermined period to another" means, for example, that radiographic images are obtained at the $1^{st}$ time phase of the $1^{st}$ period, at the $2^{nd}$ time phase of the $2^{nd}$ period, and so on until at the $n^{th}$ time phase of the $n^{th}$ period. The aforementioned referent also includes the case, for example, where eight time phases are allocated to a single period, and the radiographic images are obtained at the $1^{st}$ and $6^{th}$ time phases of the $1^{st}$ period, at the $3^{rd}$ and $8^{th}$ time phases of the $2^{nd}$ period, at the $5^{th}$ time phase of the $3^{rd}$ period, at the $2^{nd}$ and $7^{th}$ time phases of the $4^{th}$ period, and at the $4^{th}$ time phase of the $5^{th}$ period. The order of the time phases for obtaining radiographic images may be set arbitrarily. But, radiographic images may be obtained most efficiently when the time phases are allocated in equal intervals as described above.

The apparatus of the present invention may further comprise an interpolated image generating means for generating an image through interpolation from a plurality of radiographic images already obtained, which corresponds to a time phase that differs from each of the time phases at which the plurality of radiographic images was obtained.

If the apparatus of the present invention further comprises a timing setting means for setting the timing for obtaining the dynamic radiographic image on a periodical basis based on the dynamic signal, the control means described above may be configured such that the dynamic radiographic image is obtained according to the timing set by the timing setting means.

The referent of "timing for obtaining the dynamic radiographic image" as used herein means timings for obtaining radiographic images for generating the dynamic radiographic image. For example, if the dynamic radiographic image is generated from five radiographic images, the aforementioned referent means the initiation timings for obtaining the five radiographic images or the like.

If the apparatus of the present invention further comprises an unsteady state detecting means for detecting an unsteady state of the dynamic signal, the control means may be configured such that the dynamic radiographic image of the subject is obtained automatically when an unsteady state is detected by the unsteady state detecting means.

The referent of "unsteady state" as used herein means a state in which the dynamic signal is moving irregularly rather than periodically.

The subject may be a region of a living organism which is moved periodically by the cardiac beats or respiration.

According to the dynamic radiographic image obtaining method and apparatus, the dynamic signal of the subject is obtained, and a plurality of time phases is allocated to each of predetermined periods of the dynamic signal. Then, a radiographic image of the subject is obtained at a time phase that differs sequentially from one predetermined period to another, and the radiographic image obtained is stored with the time phase information correlated therewith. Thereafter, a dynamic radiographic image of the subject is obtained by arranging the radiographic images obtained in the order of the time phases, each being stored correlated with each corresponding radiographic image, from the radiographic image obtained at the time phase closest to the starting point of the predetermined periods of the dynamic signal. This ensures a sufficient time to obtain a radiographic image of the subject, and resolution of the radiographic image may be enhanced. Thus, displaying the dynamic radiographic image comprised of high resolution images on the monitor as a motion image allows the observer to perform more detailed functional diagnosis of the subject.

If the apparatus further comprises an interpolated image generating means for generating an image through interpolation from a plurality of radiographic images already obtained, which corresponds to a time phase that differs from each of the time phases at which the plurality of radiographic images was obtained, more frames may be provided for a dynamic radiographic image, and more smooth movement of the dynamic radiographic image may result when displayed on the monitor as a motion image.

Where the dynamic radiographic image is obtained on a periodical basis, the timing for obtaining the dynamic radiographic image may be set based on the dynamic signal, and the dynamic radiographic image may be obtained according to the timing signal. This allows the dynamic radiographic image to be obtained easily on a periodical basis, and user-friendliness of the apparatus may be enhanced.

When the apparatus further comprises an unsteady state detecting means for detecting an unsteady state of the dynamic signal of the subject, and the control means is configured such that a dynamic radiographic image of the subject is obtained automatically when an unsteady state is detected by the unsteady state detecting means, the apparatus may readily obtain the dynamic radiographic image of the subject under an unsteady state, and user-friendliness of the apparatus may further be enhanced.

BRIEF DESCRIPTION OF THE DRAWINGS

FIG. 5 is a schematic block diagram of the dynamic radiographic image obtaining apparatus according to a second embodiment of the present invention.

DESCRIPTION OF THE PREFERRED EMBODIMENTS

Figure 1:
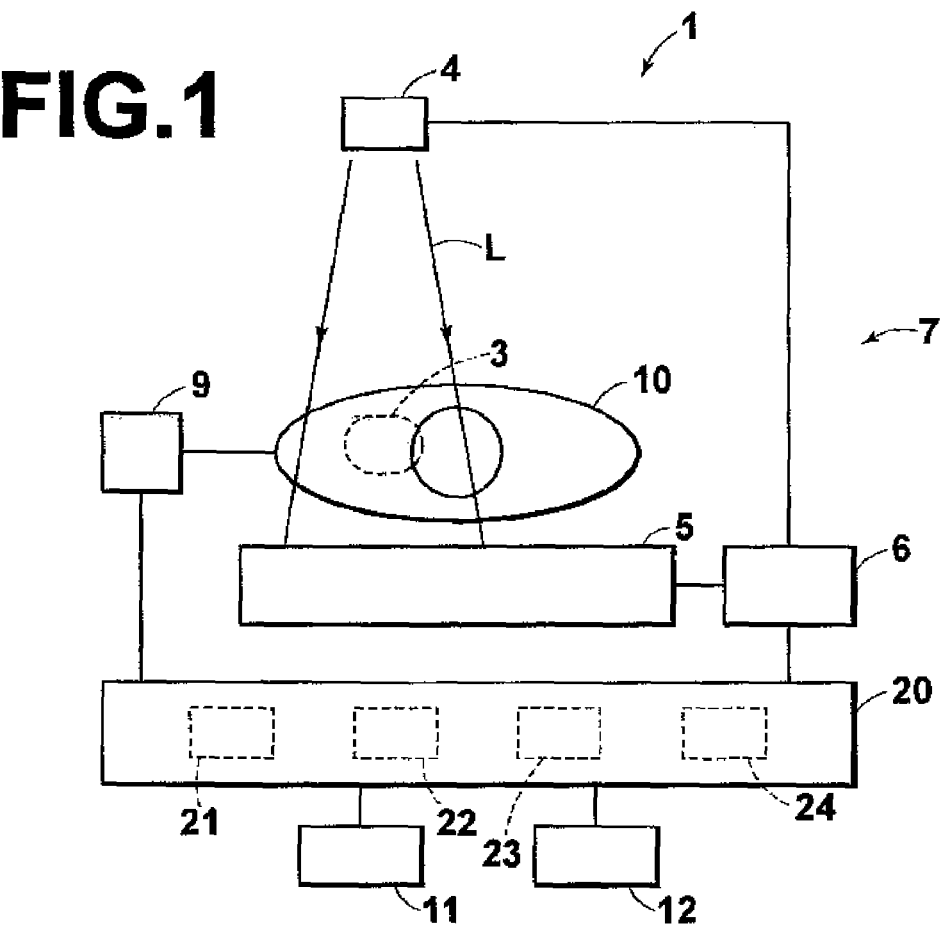
FIG. 1 is a schematic block diagram of the dynamic radiographic image obtaining apparatus according to a first embodiment of the present invention.

Hereinafter, preferred embodiments of the present invention will be described in detail with reference to accompanying drawings. FIG. 1 is a schematic block diagram of the dynamic radiographic image obtaining apparatus according to a first embodiment of the present invention. As shown in FIG. 1, the dynamic radiographic image obtaining apparatus of the present embodiment has a radiation source 4 located above the subject 3, which is the heart of an examinee 10; an image obtaining section 7 comprised of an image detector 5 located below the subject 3 and a controller 6 configured to control the image detector 5 and radiation source 4; a cardiograph 9 as a dynamic signal detecting means for detecting the dynamic signal of the subject 3; a main controller 20 connected to the controller 6 and cardiograph 9; an input 11 connected to the main controller 20; and a display 12.

X-ray L is irradiated on the subject 3 from the radiation source 4 of the image obtaining section 7. The X-ray L passed through the subject 3, which carries radiographic image information of the subject 3, is received by the image detector 5.

As for the image detector 5, an image detector of TFT reading type is used. It converts charges forming a latent image stored in the storage section to image signals by driving TFTs for scanning the recording medium, and outputs the converted image signals. Image signals outputted from the image detector 5 are outputted to the main controller 20 through the controller 6. Details of the image detector 5 including the timings for obtaining radiographic images will be described later.

The main controller 20 has an image memory 21 for storing image signals outputted from the controller 6 of the image obtaining section 7 as a radiographic image on an image by image basis; a timing signal generator 22 for outputting timing signals A1 to An to the controller 6 for obtaining radiographic images; a dynamic image generator 23 for generating a dynamic radiographic image by changing the order of the radiographic images stored in the image memory 21; and an image memory 24 for storing the dynamic radiographic image generated by the dynamic image generator 23.

Figure 2:
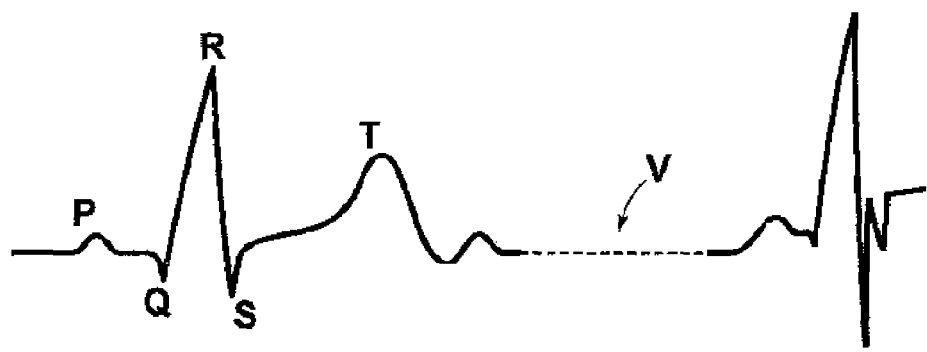
FIG. 2 is a drawing illustrating an electrocardiogram.

Hereinafter, a dynamic radiographic image obtaining process will be described. In the course of description, each component of the main controller 20 will also be described in detail. Prior to obtaining a dynamic radiographic image, electrodes of the cardiograph 9 (not shown) are attached to the examinee 10. The cardiograph 9 obtains an electrocardiogram of the examinee 10 through the electrodes, which is sent to the main controller 20. FIG. 2 shows an example of the electrocardiogram obtained by the cardiograph 9. The electrocardiogram indicates the cardiac action potential in vertical direction with the temporal change in horizontal direction. "P" wave is generated when the atria are contracted, and "QRS" wave is generated when the ventricles are contracted. "T" wave is generated when the ventricles have contracted, thereafter, a substantially constant wave "V" continues, which indicates a period of dilated ventricles, that is, it indicates that the heart is being maximally dilated.

First, the timing signal generator 22 detects average period between "R" waves from the electrocardiogram, which is designated as the cardiac beat period. The radiographer of the dynamic radiographic image sets the number of cardiac beats and required resolution through the input 11 by referring to the beat period. The number of frames of the dynamic image increases with the number of radiographic images obtained, and the motion image displayed on the monitor moves more smoothly. But when a large number of radiographic images are obtained, a sufficient reading time for the image signals forming each radiographic image is not secured, and the resolution may not be increased sufficiently. The resolution value set by the radiographer is also set in the controller 6 of the image obtaining section 7 through the main controller 20.

Hereinafter, example cases will be described. In the examples it is assumed that a required reading time for reading out the image signals corresponding to a single radiographic image with the highest resolution (high resolution) is 1 second, that with half the highest resolution is 0.6 seconds, and the beat period of the examinee is 1 second.

Figure 3:
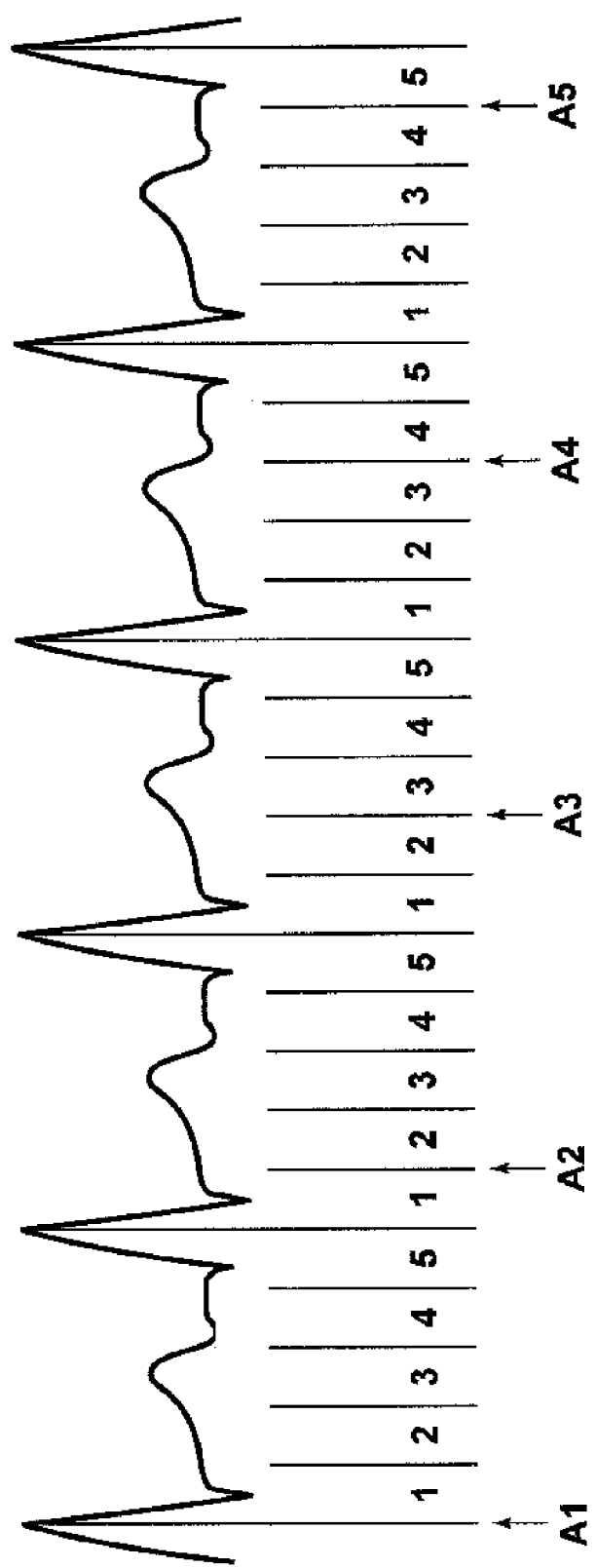
FIG. 3 is a drawing illustrating time phases allocated to an electrocardiogram.

A first example case will be described. In the example, five cardiac beats and "high resolution" are assumed to be set as the number of beats for obtaining radiographic images (image obtaining beat counts), and required resolution respectively. Preferably, the radiographic image is obtained with the examinee holding the breath. First, the image obtaining beat counts are multiplied by the beat period and divided by the reading time, that is, 5×1/1 to obtain the integer portion of the result of 5 in this case. This value of 5 is the number of time phases to be allocated to a single period. As shown in FIG. 3, five time phases, from the $1^{st}$ to $5^{th}$, are allocated to each period of 1 second. Then, the $1^{st}$ irradiation of X-ray L is performed at the starting point of the $1^{st}$ time phase of the $1^{st}$ beat, and the image signals are outputted from the image detector 5 immediately. Thereafter, the $2^{nd}$ irradiation of X-ray L is performed at the starting point of the $2^{nd}$ time phase of the $2^{nd}$ beat, which is located at the latter position by the image obtaining beat counts, in this case 5, from the immediately preceding time phase where irradiation of X-ray L took place, and the image signals are outputted. Next irradiation of X-ray L is performed at the starting point of the $3^{rd}$ time phase of the $3^{rd}$ beat, then at the starting point of the $4^{th}$ time phase of the $4^{th}$ beat, and finally at the starting point of the $5^{th}$ time phase of the $5^{th}$ beat, and image signals are outputted at respective timings. This method allows radiographic images at the $1^{st}$ to $5^{th}$ time phases to be obtained with high resolution. The interval between the irradiations of the X-ray L is 1.2 seconds, which allows image signals for a single radiographic image of high sensitivity and high resolution to be read out.

This means that the timing signal generator 22 just needs to output timing signals A1 to A5 that indicate the irradiation timings of X-ray L at an interval of 1.2 seconds.

Figure 4:
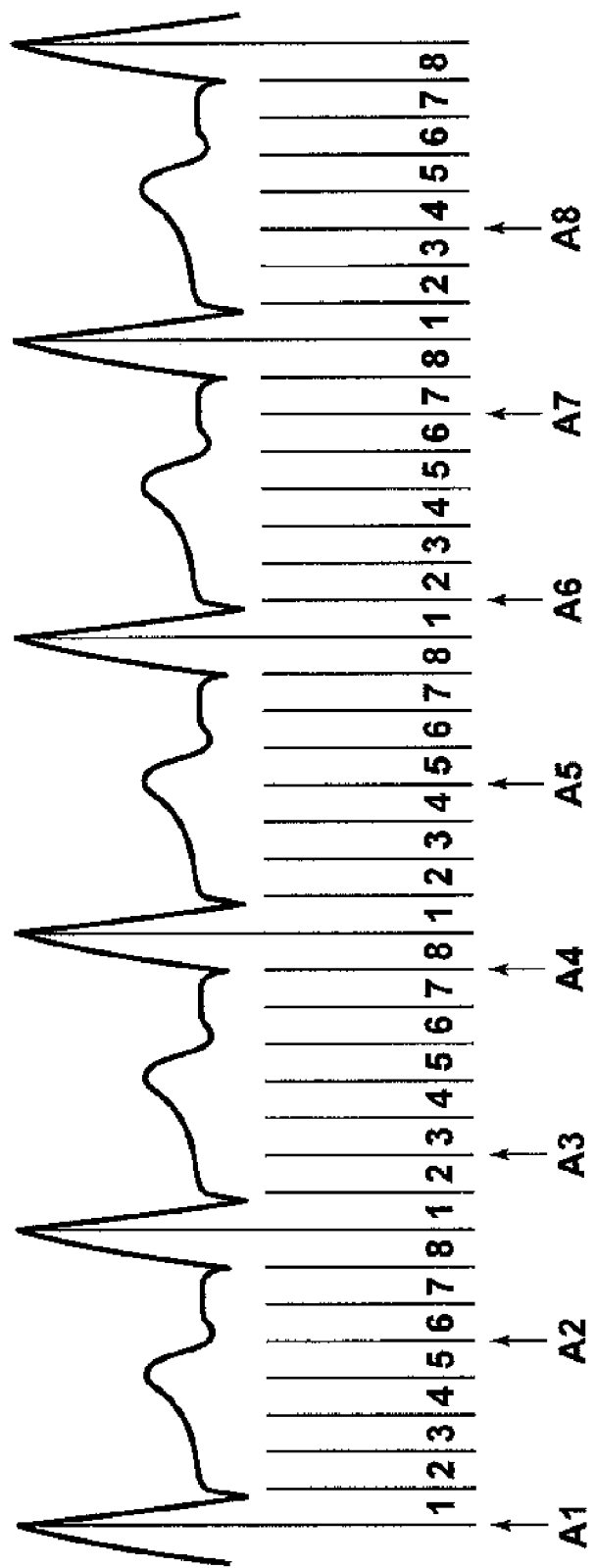
FIG. 4 is a drawing illustrating time phases allocated to an electrocardiogram.

Hereinafter, a second example case will be described. In the example, five cardiac beats and "medium resolution" are assumed to be set as the image obtaining beat counts and the required resolution respectively. First, the image obtaining beat counts are multiplied by the beat period and divided by the reading time, that is, 5×1/0.6 to obtain the integer portion of the result of 8 in this case. As shown in FIG. 4, eight time phases, from the $1^{st}$ to $8^{th}$, are allocated to each period of 1 second. Then, the $1^{st}$ irradiation of X-ray L is performed at the starting point of the $1^{st}$ time phase of the $1^{st}$ beat. Thereafter, the $2^{nd}$ irradiation of X-ray L is performed at the starting point of the $6^{th}$ time phase of the $1^{st}$ beat, which is located at a latter position by the image obtaining beat counts, in this case 5, from the immediately preceding time phase where irradiation of X-ray L took place. Next irradiation of X-ray L is performed at the starting point of the $3^{rd}$ time phase of the $2^{nd}$ beat, then at the starting point of the $8^{th}$ time phase of the $2^{nd}$ beat, at the starting point of the $5^{th}$ time phase of the $3^{rd}$ beat, at the starting point of the $2^{nd}$ time phase of the $4^{th}$ beat, at the starting point of the $7^{th}$ time phase of the $4^{th}$ beat, and finally at the starting point of the $4^{th}$ time phase of the $5^{th}$ beat. The interval between the irradiations of the X-ray L is 0.625 seconds, which allows image signals for a single radiographic image of medium resolution to be read out.

This means that the timing signal generator 22 just needs to output timing signals A1 to A8 at an interval of 0.625 seconds.

When the timing signals A1 to An for irradiating X-ray L are inputted from the timing signal generator 22, the image obtaining section 7 controls the radiation source 4 to emit X-ray L at each timing. The image detector 5 records the radiographic image information on the storage section as a latent image, converts the charges forming the latent image stored to image signals, and outputs them to the main controller 20 through the controller 6. If "high resolution" is set as the resolution of the radiographic image, image signals corresponding to all of the pixels of the radiographic image are outputted from the image detector 5. Whereas, if "medium resolution" is set as the resolution of the radiographic image, pixel skipping is performed on the radiographic image, and image signals corresponding to half of all pixels of the radiographic image are outputted from the image detector 5.

The main controller 20 stores the image signals outputted from the image detector 5 in the image memory 21 as a radiographic image on an image by image basis. When the radiographic image is stored in the image memory 21, the information that indicates the time phase at which the image was obtained is also stored in combination with the radiographic image. After images obtained at respective time phases have been stored, the dynamic image generator 23 reads out the images in the order of the time phases, that is, the radiographic image correlated with the $1^s$ time phase is read out first, then the radiographic image correlated with the $2^{nd}$ time phase and so on, and finally the radiographic image correlated with $n^{th}$ time phase is read out. Then, it restores these radiographic images in this order in the image memory 24 as a dynamic radiographic image. Thereafter, the main controller 20 displays the dynamic radiographic image stored in the image memory 24 on the display 12 as a motion image. When the dynamic radiographic image is displayed, each of the radiographic images is displayed at an interval that corresponds to that of the time phase, and the dynamic radiographic image is displayed repeatedly without interruption. Thus, the observer may observe a motion image which is analogous to the actual pounding state of the heart.

As is clear from the description above, in the dynamic radiographic image obtaining apparatus of the present embodiment, the electrocardiogram of the subject 3 is obtained to detect the period between the "R" waves appeared on the electrocardiogram. Then, a plurality of time phases are allocated to the period of 1 second, and a radiographic image of the subject 3 is obtained at a time phase in each period, which differs sequentially from one predetermined period to another. Each of the radiographic images is stored in combination with the time phase information. Then, the radiographic images obtained are arranged in the order of the time phases, each being stored correlated with each corresponding radiographic image, from the radiographic image obtained at the time phase closest to the starting point of the periods ("R" waves) to obtain the dynamic radiographic image of the subject. This ensures a sufficient time for reading out image signals forming each of the radiographic images outputted from the image detector 5, and resolution of the resulting dynamic radiographic image may be enhanced. Thus, displaying the dynamic radiographic image on the monitor as a motion image allows the observer to perform detailed functional diagnosis. In the present embodiment, the timing signals A1 to An are set such that radiographic images are obtained at equal intervals. But the apparatus of the present invention is not limited to this, and image obtaining timings may be set arbitrarily as long as radiographic images, which correspond to all of image obtaining time phases, are obtained within the desired number of cardiac beats. But, radiographic images may be obtained most efficiently if they are obtained at equal time intervals as in the present embodiment.

Hereinafter, the dynamic radiographic image obtaining apparatus 2 according to a second embodiment of the present invention will be described with reference to FIG. 5. FIG. 5 is a schematic block diagram of the dynamic radiographic image obtaining apparatus 2 of the present invention. In FIG. 5, components identical to those in the FIG. 1 are given the same reference numerals and will not be elaborated further upon here unless otherwise required.

A main controller 30 has the image memory 21; a timing signal generator 31 for outputting timing signals A1 to An to the image obtaining section 7; an unsteady state detector 32 for detecting an unsteady state of the electrocardiogram signal; a dynamic image generator 33 for generating a dynamic radiographic image by changing the order of the radiographic images stored in the image memory 21; and an image memory 35 for storing the dynamic radiographic image generated by the dynamic image generator 33.

The timing signal generator 31 outputs timing signals A1 to An for obtaining radiographic images on a periodical basis based on the value set through the input 11. It also outputs the timing signals A1 to An immediately when an unsteady state, that is, the state, in which a normal cardiac cycle appeared on the electrocardiogram being disturbed, is detected by the unsteady state detector 32.

The dynamic image generator 33 generates a dynamic radiographic image by changing the order of the radiographic images stored in the image memory 21. It has an interpolated image generator 34 for generating an image through interpolation from two radiographic images obtained at two successive time phases, which corresponds to the intermediate time phase between the two successive time phases. Thus, it generates an interpolated dynamic radiographic image by combining the radiographic images obtained by imaging and interpolated radiographic images obtained through interpolation.

Hereinafter, a dynamic radiographic image obtaining process will be described. In the course of description, each component of the main controller 30 will also be described in detail.

The timing signal generator 31 detects average period between "R" waves from the electrocardiogram, which is designated as the cardiac beat period.

The radiographer of the dynamic radiographic image sets the number of cardiac beats and required resolution through the input 11 by referring to the beat period. At the same time, if the dynamic radiographic image obtaining process is repeated on a periodical basis, for example, every 120 beat periods, the beat period information is also inputted. The radiographer also selects either "normal dynamic radiographic image generating mode" or "interpolated dynamic radiographic image generating mode", which will be described later.

The timing signal generator 31 calculates number of cardiac beats from the electrocardiogram, and outputs timing signals A1 to An at every 120 beat periods set by the radiographer. Preferably, an announcing signal, such as a buzzer, is provided to notify the examinee 10 of the initiation of imaging at the time when 115 cardiac beats are detected so that the examinee 10 may hold the breath for imaging. The timing signal generator 31 outputs timing signals A1 to An immediately when an unsteady state, such as irregular pulses, is detected on the electrocardiograph.

When the timing signals A1 to An are inputted from the timing signal generator 31, the image obtaining section 7 obtains radiographic images, and outputs the image signals to the main controller 30.

The main controller 30 stores the image signals outputted from the image obtaining section 7 in the image memory 21 as a radiographic image on an image by image basis in combination with the time phase information. After images obtained at the timings indicated by the timing signals A1 to An have been stored, and if "dynamic radiographic image generating mode" is selected, the dynamic image generator 33 sequentially reads out the image combined with the $1^{st}$ time phase, the image combined with the $2^{nd}$ time phase, and so on until the image combined with $n^{th}$ time phase. Then, it restores these radiographic images in this order in the image memory 35 as a dynamic radiographic image. If "interpolated dynamic radiographic image generating mode" is selected, the interpolated image generator 34 generates an image through interpolation from two radiographic images obtained at two successive time phases, which corresponds to the intermediate time phase between the two successive time phases. For example, where 5 radiographic images corresponding to the $1^{st}$ to $5^{th}$ time phases have been obtained, the interpolated image generator 34 generates an image through interpolation from the image corresponding to the $1^{st}$ time phase and that corresponding to the $2^{nd}$ time phase, which corresponds to the intermediate time phase (designated as $1.5^{th}$ time phase for convenience) between the two time phases. More specifically, an image corresponding to the $1.5^{th}$ time phase may be obtained, for example, by morphing with point warping method in which a multitude of corresponding points are selected from two images to change the shape step by step. Interpolated radiographic images corresponding to the $2.5^{th}$, $3.5^{th}$, $3.5^{th}$, $4.5^{th}$ and $5.5^{th}$ time phases are generated in the same manner. Thereafter, the radiographic images obtained by imaging, and the interpolated images obtained through the interpolation are arranged in the order of the $1^{st}$ time phase, $1.5^{th}$ time phase, $2^{nd}$ time phase, $2.5^{th}$ time phase, and so on to $5^{th}$ and $5.5^{th}$ time phases to generate an interpolated dynamic radiographic image, which is stored in the image memory 35. When generating an interpolated image using the morphing technique or the like from two images corresponding to two time phases, an interpolated image corresponding to any time phase within the two time phases may be generated.

The main controller 30 displays the dynamic radiographic image or interpolated dynamic radiographic image stored in the image memory 35 on the display 12 as a motion image. When the dynamic radiographic image is displayed, each of the radiographic images is displayed at an interval that corresponds to that of the time phase, and when the interpolated dynamic image is displayed, each of the radiographic images and of interpolated radiographic images are displayed at an interval that corresponds to ½ of that of the time phase, and the dynamic radiographic image is displayed repeatedly without interruption. Thus, the observer may observe a motion image which is analogous to the actual pounding state of the heart.

As is clear from the description above, the dynamic radiographic image obtaining apparatus according to the present invention may provide the identical effects provided by the apparatus according to the first embodiment. In addition, the apparatus of the present embodiment has an interpolated image generator 34 for generating an image through interpolation from a plurality of radiographic images obtained by imaging, which corresponds to the intermediate time phase between the time phases at which the plurality of radiographic images was obtained. Thus, more frames may be provided for the interpolated dynamic radiographic image, and more smooth movement of the dynamic radiographic image may result when displayed on the monitor as a motion image.

Where a dynamic radiographic image is obtained on a periodical basis, the timing for obtaining the dynamic radiographic image is set based on the electrocardiogram, and the dynamic radiographic image is obtained based on the timing signal. This allows the radiographic image to be obtained easily on a periodical basis, and user-friendliness of the apparatus may be enhanced.

Furthermore, when an unsteady state is detected on the electrocardiogram, a dynamic radiographic image is obtained automatically. Thus, the apparatus of the present invention may readily obtain a dynamic radiographic image of the subject under an unsteady state, and user-friendliness of the apparatus may further be enhanced.

Preferably, when storing a radiographic image, the electrocardiogram information is stored in combination with the radiographic image, in addition to the time phase information that indicates the time phase at which the X-ray L was emitted. After radiographic images of all the time phases have been obtained, if a discrepancy is found between the time phase at which the radiographic image was actually obtained and the time phase stored in combination with the radiographic image when comparison is made between the timings at which the radiographic images were obtained and the electrocardiogram, or if a radiographic image has not been obtained, an appropriate interpolated radiographic image may be generated for use through the interpolated image generator 34.

In the embodiments, description has been made by way of examples in which a dynamic radiographic image of the heart is obtained. But the present invention is not limited to this. For example, a dynamic radiographic image of a blood vessel or the like may also be obtained. In addition, in the embodiments, an electrocardiograph is used, and the cardiac beat information is obtained from the electrocardiogram. But, a plethysmograph may be used instead of the electrocardiograph. As for the plethysmograph, various types may be used, including photoelectric type, piezoelectric type, pulse oxiometer, accelerated plethysmograph, or the like.

Furthermore, a dynamic radiographic image of a subject that moves regularly by respiration, such as the lungs or the like, may also be obtained. In this case, a respiration monitoring belt, optical camera, spirometer, or pulmometer may be used as the dynamic signal detecting means for detecting the dynamic state of respiration.

Still Further, the present invention may be applied for obtaining a dynamic radiographic image of an automobile engine or the like. A dynamic radiographic image of a part of an automobile which is moving periodically, such as inside of the engine or the like, may be obtained by detecting the external movements, such as those of the cranks, shafts and the like, through known optical or electromagnetic means.

What is claimed is:

1. A dynamic radiographic image obtaining apparatus for obtaining a dynamic radiographic image of a periodically moving subject, the apparatus comprising:
   a dynamic signal detecting means for detecting a dynamic signal of the subject;
   an image obtaining means for obtaining a plurality of radiographic images of the subject by irradiating radiation on the subject from one direction and detecting the radiation passed through the subject;
   a control means for allocating a plurality of time phases to each of predetermined periods of the dynamic signal detected by the dynamic signal detecting means, and controlling the image obtaining means such that the radiographic images of the subject are obtained at respective time phases that differ from one predetermined period to another;
   a storing means for storing the radiographic images obtained with time phase information and the dynamic signal which was detected during obtainment of the radiographic image correlated therewith; and
   a dynamic image generating means for selecting between modes of obtaining radiographic images, said modes including a dynamic radiographic mode wherein the radiographic image is a series of images coordinated with the plurality of time phases in order, which are correlated and stored with the radiographic image, said modes further including an interpolated image generating mode, wherein an interpolated image generating means interpolates the plurality of obtained radiographic images of adjacent time phases corresponding to the time phase represented by the time phase information and for arranging the selected radiographic images in the order of the time phases, each being stored and correlated with each corresponding radiographic image among the radiographic images, from a radiographic image obtained at a time phase closest to a starting point of the each of the predetermined periods of the dynamic signal.

2. The dynamic radiographic image obtaining apparatus according to claim 1, wherein the apparatus further comprises a timing setting means for setting timing for obtaining the dynamic radiographic image on a periodical basis based on the dynamic signal, and the control means is configured such that the dynamic radiographic image is obtained according to the timing set by the timing setting means.

3. The dynamic radiographic image obtaining apparatus according to claim 2, wherein the apparatus further comprises an unsteady state detecting means for detecting an unsteady state of the dynamic signal, and the control means is configured such that the dynamic radiographic image is obtained automatically when an unsteady state of the dynamic signal is detected by the unsteady state detecting means.

4. The dynamic radiographic image obtaining apparatus according to claim 3, wherein the subject is a region of a living organism which moves periodically by cardiac beats or respiration.

5. The dynamic radiographic image obtaining apparatus according to claim 2, wherein the subject is a region of a living organism which moves periodically by cardiac beats or respiration.

6. The dynamic radiographic image obtaining apparatus according to claim 1, wherein the apparatus further comprises an unsteady state detecting means for detecting an unsteady state of the dynamic signal, and the control means is configured such that the dynamic radiographic image is obtained automatically when an unsteady state of the dynamic signal is detected by the unsteady state detecting means.

7. The dynamic radiographic image obtaining apparatus according to claim 6, wherein the subject is a region of a living organism which moves periodically by cardiac beats or respiration.

8. The dynamic radiographic image obtaining apparatus according to claim 1, wherein the subject is a region of a living organism which moves periodically by cardiac beats or respiration.

9. The dynamic radiographic image obtaining apparatus according to claim 1, wherein the dynamic signal of the subject is a cardiac beat signal and the each of the predetermined periods is a period between cardiac beats.

10. The dynamic radiographic image obtaining apparatus according to claim 1, wherein the interpolated image generating means employs a morphing with point warping method.

11. The dynamic radiographic image obtaining apparatus according to claim 1, wherein when the interpolated image generating mode is selected, the interpolated image generating means outputs radiographic image data at corresponding time phases in sequence with the interpolated images obtained between adjacent time phases.

* * * * *